United States Patent [19]

Andrus et al.

[11] Patent Number: 5,137,884
[45] Date of Patent: Aug. 11, 1992

[54] N-TETRAZOLYL BETA-LACTAMS

[75] Inventors: W. Alexander Andrus, Fanwood; Burton G. Christensen, Cliffside Park; James V. Heck, Fanwood, all of N.J.

[73] Assignee: Merck & Co., Inc., Rahway, N.J.

[21] Appl. No.: 552,570

[22] Filed: Nov. 16, 1983

[51] Int. Cl.[5] .................. C07D 401/14; C07D 417/14; C07D 403/04; A61K 31/44
[52] U.S. Cl. .................................. 514/210; 540/363; 540/364; 548/251
[58] Field of Search .................. 260/245.4; 546/275; 424/244, 263; 540/363, 364; 514/210

[56] References Cited
FOREIGN PATENT DOCUMENTS
68-466 6/1982 European Pat. Off. .

OTHER PUBLICATIONS
Derwent Abstract J6 0013 787A Toyama Chem. KK.
Klich et al Tetrahedron Letters, 25, 3849–3852 (1984).
Teutch Abstract #843 of the 1986 ICAAC (p. 252).
Derwent Abstract for aP114128 (1984).
Andrus et al Chem Abs 100, 209481K.
Derwent Patent Abstract 84325 D/46-BO3-SAGA 7.03.80 for Japan 56-125,360.

*Primary Examiner*—Mark L. Berch
*Attorney, Agent, or Firm*—Raymond M. Speer; Hesna J. Pfeiffer

[57] ABSTRACT

N-tetrazolyl beta-lactams of the Formula:

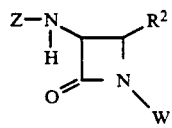

and the pharmaceutically acceptable salts thereof wherein $R^2$ is hydrogen, alkyl having 1 to 6 carbon atoms or carboalkoxy having 2 to 7 carbon atoms; and Z is

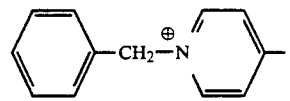

and W is

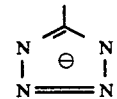

thus forming a zwitterion,
or Z is

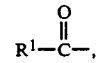

wherein $R^1$ is benzyl, phenyloxymethyl or

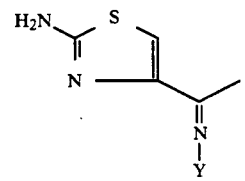

wherein
Y is alkoxy or substituted alkoxy having 1 to 6 carbon atoms wherein the substituent on the alkoxy group is —COOH; and
W is

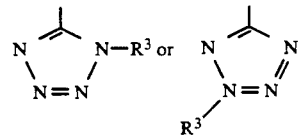

wherein $R^3$ is H, M or —CH$_2$COOM, wherein M is a pharmaceutically acceptable cation are disclosed. The compounds are useful as antibiotics.

6 Claims, No Drawings

N-TETRAZOLYL BETA-LACTAMS

N-tetrazolyl beta-lactams of the Formula:

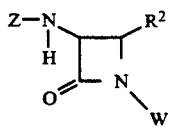

and the pharmaceutically acceptable salts thereof wherein $R^2$ is hydrogen, alkyl having 1 to 6 carbon atoms or carboalkoxy having 2 to 7 carbon atoms; and Z is

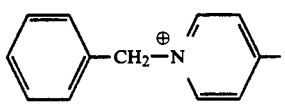

and W is

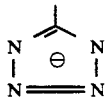

thus forming a zwitterion, or Z is

wherein $R^1$ is benzyl, phenyloxymethyl or

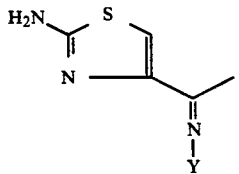

Y is alkoxy or substituted alkoxy having 1 to 6 carbon atoms wherein the substituent on the alkoxy group is —COOH; and W is

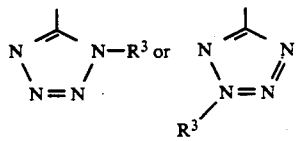

wherein $R^3$ is H, M or —CH$_2$COOM, wherein M is a pharmaceutically acceptable cation (e.g. sodium, potassium or magnesium, preferably sodium or potassium. If M is a divalent cation, M may be shared by two W groups.

Illustrative examples of compounds of the present invention are the following:

(3S, 4S)-4-methyl-3-[(Z)-2-(2-aminothiazol-4-yl)-2-(2-carboxyprop-2-oxyimino)acetamido]-1-(5-tetrazolyl)-azetidin-2-one;

4S-methyl-3S-(2-(2-aminothiazol-4-yl)-2-(Z)-methoxyiminoacetamido)-1-(5-tetrazolyl)-azetidin-2-one;

3S-(2-(2-aminothiazol-4-yl)-2-(Z)-methoxyimminoacetamido)-1-(5-tetrazolyl)-azetidin-2-one;

Potassium 1-(5-tetrazolyl)-3S-phenylacetamidoazetidin-2-one;

4S-methyl-3S-[(l-benzylpyridinium)-4-amino]-1-5-tetrazolyl)-azetidin-2-one; and

3S-[(1-benzylpyridinium)-4-amino]-1-(5-tetrazolyl)-azetidin-2-one;

Potassium 3S-phenylacetamido-1-[(5-tetrazolyl)-1-acetate)]-azetidin-2-one; and

Potassium 3S-phenylacetamido-1-[(tetrazolyl-(2-acetate)]-azetidin-2-one.

Preferred compounds of the present invention are the following:

(3S, 4S)-4-methyl-3-[(Z)-2-(2-aminothiazol-4-yl)-2-(2-carboxyprop-2-oxyimino)acetamido]-1-(5-tetrazolyl)-azetidin-2-one;

4S-methyl-3S-(2-(2-aminothiazol-4-yl)-2-(Z)-methoxyiminoacetamido)-1-(5-tetrazolyl)-azetidin-2-one;

3S-(2-(2-aminothiazol-4-yl)-2-(Z)-methoxyimminoacetamido)-1-(5-tetrazolyl)-azetidin-2-one;

Potassium 1-(5-tetrazolyl)-3S-phenylacetamidoazetidin-2-one;

4S-methyl-3S-[(l-benzylpyridinium)-4-amino]-1-(5-tetrazolyl)-azetidin-2-one; and 3S-[(1-benzylpyridinium)-4-amino]-1-(5-tetrazolyl)-azetidin-2-one.

Particularly preferred compounds of the present invention are the following: (3S, 4S)-4-methyl-3-[(Z)-2-(2-aminothiazol-4-yl)-2-(2-carboxyprop-2-oxyimino)acetamido]-1-(5-tetrazolyl)-azetidin-2-one;

4S-methyl-3S-(2-(2-aminothiazol-4-yl)-2-(Z)-methoxyiminoacetamido)-1-(5-tetrazolyl)-azetidin-2-one;

3S-(2-(2-aminothiazol-4-yl)-2-(Z)-methoxyimminoacetamido)-1-(5-tetrazolyl)-azetidin-2-one.

The compounds of the present invention may be prepared from an appropriate N-tert-butoxycarbonyl amino acid, for example, N-Boc-L-serine ($R^2$=H) or N-Boc-L-threonine ($R^2$=CH$_3$). The aforementioned amino acids have the preferred chirality at the C-3 (serine) and C-3 and C-4 sites (threonine). The amino and carboxyl funtionalities allow convenient handles for introduction of various acyl side chains and the 5-amino tetrazole group respectively. The preparation of potassium 3S-phenylacetamido-1-(5-tetrazolyl)azetidin-2-one 11 from N-Boc-L-serine is set forth in the following scheme and illustrates the preparation of compounds of the present invention:

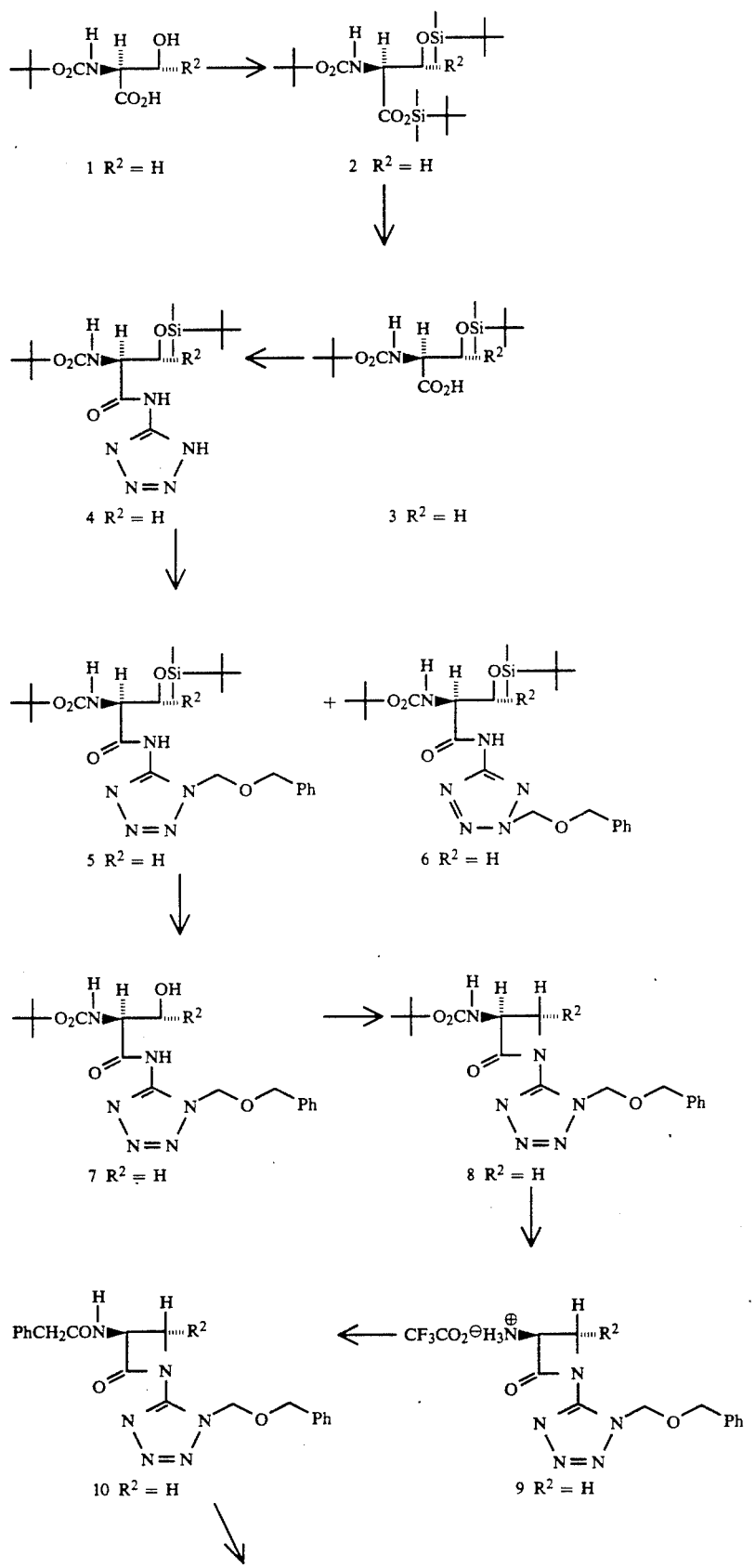

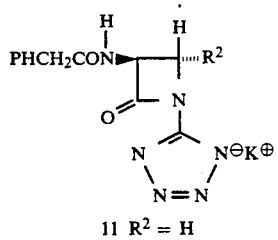

11 R² = H

When coupling N-Boc-L-serine with 5-amino tetrazole it is generally expedient to first protect the hydroxyl as its tert-butyldimethylsilyl ether (3) to increase the yield and ease of product isolation in the coupling reaction. The carbodiimide or mixed anhydride methods give comparable yields of 4. For a discussion of these methods, see "The Peptides", Vol. I, E. Gross and J. Meienhofer, Editors, Academic Press, New York, N.Y., 1979, pages 242–262 and 264–314, respectively, these disclosures being hereby incorporated herein by reference. Both methods may generally be used when R² is other than hydrogen. Since subsequent reactions generally require the tetrazole to be blocked, 4 is alkylated to attach a hydrogenolytically removable group with a reagent such as chloromethylbenzylether. Use of the latter gives a mixture of the 1-isomer 5 and the 2-isomer 6 in a 1 to 1 ratio. Substituting bis-tri-butyltinoxide for triethylamine in the aforementioned alkylation gives an isomer ratio for 5 to 6 of 2.5 to 1. Compounds 5 and 6 may then be subjected to the further reactions discussed with reference to 5. Compound 5 may be desilylated by treatment with 48% hydrogen fluoride in acetonitrile to give 7. Ring closure of 7 by the dialkylazodicarboxylate/triphenylphosphine method gives 8. For a discussion of this method, see P. G. Mattingly, J. F. Kerwin, M. J. Miller, J. Am. Chem. Soc, 101, 3983 (1979), this disclosure being hereby incorporated herein by reference. There is considerable latitude amongst the reagents giving a successful ring closure. Carbon tetrachloride may be substituted for triphenylphosphine and diethyl, diisopropyl- or dimethylazodicarboxylates may be used. Side chain introduction may be effected by trifluoroacetic acid removal of tert-butyloxycarbonyl to yield 9 and acylation of 9 by phenylacetylchloride to give 10. Other side chains are similarly introduced by standard methods. For example, the side chain acid and the 3-aminoazetidin-2-one may be coupled by chlorodiphenylphosphate/triethylamine or isobutylchloroformate/N-methylmorpholine. Compound 10 may be subjected to hydrogenolysis with palladium catalysis to give 11, which may be isolated with reverse-phase preparative TLC (thin layer chromatography).

Preparation of compounds where R² is carboalkoxy is illustrated by using malic acid as the starting material, proceding to compound 3 (page 4) according to the method of Miller et al. (J. Org. Chem. 47, 4928–4933 (1982), the disclosure of which is hereby incorporated herein by reference) and then following the steps set forth above.

Preparation of compounds where the tetrazole group is substituted with —CH₂COOM is illustrated by alkylating 4 or 24 (Example 20) with bromobenzylacetate in the presence of base hydrogenolysis of the benzyl group which furnishes compounds such as 17 and 21.

The products of this invention form a wide variety of pharmaceutically acceptable salts such as acid addition salts, e.g., with hydrochloric, hydrobromic, sulfuric, nitric, toluene-p-sulphonic and methane sulphonic acids. The salts of this invention are pharmaceutically acceptable non-toxic derivatives which can be used as the active ingredient in suitable unit-dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention may therefore be used as antibacterial drugs for treating infections caused b gram-positive or gram-negative bacteria, for example, against *Staphylococcus aureus, Escherichia coli, Klebsiella pneumoniae, Serratia marcesans, Salmonella typhimurium, Pseudomonas aeruginosa, Streptococcus faecalis, Ent. aerogenes, Ent. cloacae* and *Proteus vulgaris*. The antibacterials of the invention may further be utilized as additives to animal feeds, for preserving foodstuffs and as disinfectants. For example, they may be employed in aqueous compositions in concentrations ranging from 0.1 to 100 parts of antibiotic per million parts of solution in order to destroy and inhibit one growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. They may be combined with other drugs to provide compositions having a broad spectrum of activity. These antibiotics may be employed in capsule form or as tablets, powders or liquid solutions or as suspensions or elixirs. They may be administered orally, topically or parenterally by injection (intravenously or intramuscularly).

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, cornstarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspensions, solutions, emulsions, syrups, elixirs, etc. or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example, methyl or propyl p-hydroxybenzoates or sorbic acid. Suppositories will contain conventional suppository base, e.g. cocoa butter or other glycerides.

Compositions for injection may be presented in unit dose form in ampules, or in multidose containers with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition and size of the subject being treated as well as the route and frequency of administration, the parenteral route being preferred for generalized infections and the oral route for intestinal infections. Another factor influencing the precise dosage regimen, apart from the nature of the infection and peculiar identity of the individual being treated, is the molecular weight of the chosen species of this invention. In general, a daily oral dosage consists of from about 2 to about 600 mg of active ingredient per kg of body weight of the subject in one or more applications per day. A preferred daily dosage for adult humans lies in the range of from about 15 to 150 mg of active ingredient per kg of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 to 60%. The composition will generally contain from about 15 mg to about 1500 mg of the active ingredient; however, in general, it is preferable to employ a dosage amount in the range of from about 100 mg to 1000 mg. In parenteral administration the unit dosage is usually the pure compound in a sterile water solution or in the form of a soluble powder intended for solution. Consideration of individual properties of solubility and stability well determine the optimum pH of such a solution. The pH will generally be in range of 5.5 to 8.2.

The following Examples illustrate but do not limit the product, process, compositional or method of treatment aspect of the present invention. All temperatures are in °C.

EXAMPLE 1

Preparation of tert-butyldimethylsilyl-3-tert-butyldimethylsilyloxy-2S-tert-butyloxycarbonylamino-propanoate (2)

A mixture of N-tert-butyloxy-L-serine 1 (2.33 g, 0.0114 mol), tert-butyldimethylchlorosilane (3.60 g, 0.024 mol), imidazole (1.90 g, 0.0285 mol), and 20 ml dry N,N-dimethylformamide was stirred as a turbid suspension at room temperature for 18 hours. After the solvent was removed under vacuum, the residue was diluted with 200 ml diethylether and washed with solutions of 5% potassium dihydrogenphosphate and saturated sodium chloride. The organic phase was dried over magnesium sulfate, filtered, and evaporated under vacuum to give 4.84 (98%) 2 as a clear, mobile oil:

$^1$H NMR (CDCl$_3$) δ: 5.38 (1H, br d), 4.29 (1H, m), 4.06 (1H, dd, J=2,11), 3.89 (1H, dd, J=3,11), 1.45 (9H, s), 0.93 (9H, s), 0.86 (9H, s), 0.28 (6H, s), 0.05 (6H, s).

EXAMPLE 2

Preparation of 3-tert-butyldimethylsilyloxy-2S-tert-butyloxycarbonylamino-propanoic acid (3)

A solution of 2 (4.84 g, 0.0112 mol), 20 ml methanol, 5 ml water, and 2 ml acetic acid was stirred at room temperature for 3 hours. After the solvent was removed under vacuum, the residue was diluted with 200 ml ethyl acetate and washed with two 100 ml solutions of 5% potassium dihydrogenphosphate. The organic phase was dried over magnesium sulfate, filtered, and evaporated under vacuum to give 3.25 (91%) 3 as a clear, viscous oil:

IR(CHCl$_3$): 3450, 1715, 1675, cm$^{-1}$.

$^1$H NMR (CDCl3) δ:6.00 (1H, d, J=7), 4.42 (1H, m), 4.16 (1H, dd, J=1,11), 3.87 (1H, dd, J=2.11), 1.49 (9H, s), 0.90 (9H, s), 0.09 (6H, s).

EXAMPLE 3

Preparation of 3-tert-butyldimethylsilyloxy-2S-tertbutyloxycarbonylamino-(5-tertrazolyl)propanamide (4)

Dicyclohexylcarbodiimide (0.50 g, 2.45 mmol) was added to a mixture of 3 (0.71 g, 2.23 mmol), 1-hydroxybenzotriazole (0.60 g, 4.46 mmol), 5-aminotetrazole (0.21 g, 2.45 mmol), and 4 ml N,N-dimethylformamide. After 18 hours stirring at room temperature, 10 ml ethylacetate was added. The mixture was filtered, washing the filter cake with 10 ml ethyl acetate. The filtrate was diluted with 100 ml ethyl acetate and 100 ml diethylether then washed with solutions of 1% sulfuric acid and saturated sodium chloride. The organic phase was dried over magnesium sulfate, filtered and evaporated under vacuum. The semi-solid residue was triturated with dichloromethane to cause crystallization of 1-hydroxybenzotriazole (0.29 g), which was filtered off. The filtrate was concentrated and hexane was added, causing crystallization of 0.35 gm (41%) 4- as a white solid, m.p. 152°-55°:

$[\alpha]_{25}^D = +2.8°$(C=1, CH$_3$OH)

IR (CH$_3$CN): 3300, 1720, 1600 cm$^{-1}$.

1H NMR (CDCl3) δ:6.19 (1H, d, J=7), 4.56 (1H, m), 4.28 (1H, dd, J=3, 10.5), 3.97 (1H, dd, J=4, 10.5), 1.43 (9H, s), 0.80 (9H, s), 0.04 (6H, s).

EXAMPLE 4

Preparation of 3-tert-butyldimethylsilyloxy-2S-tert-butyloxycarbonylamino-[5-(1-benzyloxymethyl)tetrazolyl]propanamide (5) and 3-tert-butyldimethylsilyloxy-2S-tert-butyloxycarbonylamino-[5-(2-benzyloxymethyl)tetrazolyl]propanamide (6)

A mixture of 4 (0.74 g, 1.92 mmol), benzylchloromethylether (0.33 ml, 2.30 mmol), triethylamine (0.37 ml, 2.69 mmol), and 8 ml dry acetonitrile was stirred at room temperature for 18 hours, forming a white precipitate. After dilution with 200 ml diethylether and washing with solutions of 1% sulfuric acid, saturated sodium bicarbonate, and saturated sodium chloride, the organic phase was dried over magnesium sulfate, filtered, and evaporated under vacuum to give a viscous oil. Chromatography on silica gel separated the more polar, 1-isomer 0.31 g (32%) 5 from the less polar, 2-isomer 0.28 g (29%) 6 as clear oils:

5 1H NMR (CDCl3) δ:9.60 (1H, m), 7.40 (5H, br s), 5.91 (2H, s), 5.45 (1H, broad), 4.58 (1H, s), 4.42 (1H, m), 4.17 (1H, dd, J=4,10), 3.91 (1H, dd, J=6.5,10), 1.50 (9H, s), 0.92 (9H, s), 0.02 (6H,s).

EXAMPLE 5

Preparation of 3-hydroxy-2S-tert-butyloxycarbonylamino-[5-(1-benzyloxymethyl)tetrazolyl]propanamide (7)

To a solution of 5 (0.751 g, 1.48 mmol) and 30 ml dry tetrahydrofuran was added tetra-n-butylammonium fluoride (2.7 ml, 2.7 mmol, 1M in tetrahydrofuran). After being stirred at room temperature for 24 hours, the solution was diluted with 150 ml ethylacetate and washed with solutions of 1% sulfuric acid, saturated sodium bicarbonate, and saturated sodium chloride. The organic phase was dried over magnesium sulfate, filtered, and evaporated under vacuum. The brown oil was chromatographed on silica gel to give 0.516 g (89%) 7 as a crisp, white foam:

1H NMR (CDCl3) δ: 7.38 (5H, m), 5.87 (2H, s), 4.58 (2H, s), 4.45 (1H, m), 4.22 (1H, m), 3.81 (1H, m), 1.47 (9H, s).

EXAMPLE 6

Preparation of 3S-tert-butyloxycarbonylamino-1-[5-(1-benzyloxymethyl)tetrazolyl]acetidin-2-one (8)

Diisopropylazodicarboxylate (0.21 ml, 1.15 mmol) was added to a solution of 7 (0.410 g, 1.04 mmol), triphenylphosphine (0.301 g, 1.15 mmol), and 50 ml dry tetrahydrofuran at 0°. The solution was allowed to warm to room temperature and stir for 18 hours. The solvent was removed under vacuum and the residue was chromatographed on silica gel to give 0.276 g (71%) 8 as a white solid, m.p. 113°-15°:

[α]$_D^{25}$ = $^{30}$83.1 (C=1, CHCl3)
IR (CHCl3) 3450, 1790, 1700 cm$^{-1}$.
1H NMR (CDCl3)δ: 7.36 (5H, m), 6.33 (1H, d, J=ll), 6.04 (1H, d, J=ll), 4.64 (2H, s), 4.10 (2H, m), 1.45 (9H, s)

EXAMPLE 7

Preparation of trifluoroacetate, 3S-ammonium-1-[5-(1-benzyloxymethyl)tetrazolyl]azetidin-2-one (9)

Trifluoroacetic acid (2 ml) was added to a solution of 8 (0.243 g, 0.65 mmol) and 5 ml dichloromethane at −15°. The solution was allowed to warm to room temperature and stir for 3 hours. The volatiles were removed under a stream of nitrogen and under vacuum. Several milliliters of toluene were added to the residue and evaporated under vacuum. After repeating this toluene treatment twice more, 300 mg 9 remained as a viscous oil:

1H NMR (acetone d6)δ: 7.38 (5H, s), 6.06 (2H, s), 4.75 (2H, s), 4.68 (1H, m), 4.45 (2H, m).

EXAMPLE 8

Preparation of 3S-phenylacetamido-1-[5-(1-benzyloxymethyl)tetrazolyl]azetidin-2-one (10)

Pyridine (0.26 ml, 3.25 mmol) was added to a solution of 9 (0.30 g, 0.65 mmol) and 10 ml dry dichloromethane at −15°. Phenylacetychloride (0.12 ml, 0.91 mmol) was added and the solution was allowed to warm to room temperature and stir for 3 hours. Dilution with 100 ml ethyl acetate was followed by washing with 10% sodium bisulfate, saturated sodium bicarbonate, and saturated sodium chloride. The organic phase was dried over magnesium sulfate, filtered, and evaporated under vacuum. The residue was chromatographed on silica gel to give 0.143 g (56% from 8) 10 as a white solid:

IR (CHCl3): 3410, 1785, 1710 cm$^{-1}$.
1H NMR (CDCl3)δ: 7.36 (5H, m), 6.28 (1H, d, J=7), 5.86 (2H, s), 5.10 (1H, td, J=3.5, 6, 7), 4.67 (2H, s), 4.16 (1H, dd, J=6.6), 3.96 (1H, dd, J=3.5, 6), 3.67 (2H, s).

EXAMPLE 9

Preparation of potassium 3S-phenylacetamido-1-(5-tetrazolyl)azetidin-2-one (11)

A mixture of 10 (0.051 g, 0.13 mmol), 80 mg 10% palladium on carbon, 3 ml tetrahydrofuran, 2 ml ethanol, 2 ml water, and 0.5 ml pH 7, 0.1M potassium dihydrogenphosphate/dipotassium hydrogenphosphate buffer was hydrogenated at 45 psi hydrogen for 3 hours. The mixture was filtered, washing with water, and washed with 30 ml ethyl acetate/diethyl ether: 1/1. The aqueous phase was concentrated under vacuum to a 1 ml volume. Reverse-phase preparative thin layer chromatography (10% ethanol in water) allowed isolation of a single band, eluted with 20 ml acetonitrile/water: 4/1. Concentration of the eluate to 2 ml volume and lyophilization gave 0.017 g (42%)11 as a white solid:

1H NMR (D2O)δ: 7.35 (5H, m), 5.05 (1H, dd, J=3,6), 4.11 (1H, dd, J=6,6), 3.90 (1H, dd, J=3,6), 3.67 (2H, s).

EXAMPLE 10

Preparation of 3-tert-butyldimethylsilyloxy-2S-tertbutyloxycarbonylamino-[5-(1-benzylacetate)tetrazolyl]propanamide (12) and 3-tert-butyldimethylsilyloxy-2S-tert-butyloxycarbonylamino-[5-(2-benzylacetate)tetrazolyl]propanamide (13)

Triethylamine (0.22 ml, 1.58 mmol) was added to a mixture of 4 (0.463 g, 1.20 mmol), bromobenzylacetate (0.33 g, 1.44 mmol), and 5 ml dry dimethylformamide. A white precipitate formed while the mixture was stirred at room temperature for 18 hours. Dilution with 75 ml ethyl acetate and washing with solutions of 10% sodium bisulfate, 5% potassium carbonate, and saturated sodium chloride was followed by drying over magnesium sulfate and filtration. After the solvent was removed under vacuum, the residue was chromatographed on silica gel to give 0.380 g (59%) 13, as the less polar isomer, and 0.102 g (16%) 12 as the more polar isomer; each as viscous, colorless oils:

13:

IR (CHCl$_3$): 3405, 1760, 1715, 1555 cm$^{-1}$.

$^1$H NMR (CDCl$_3$) : 7.40 (5H, m), 5.46 (2H, s), 5.24 (2H, s), 4.40 (1H, m), 4.18 (1H, dd, J=4,0), 3.76 (1H, dd, J=7,10), 1.50 (9H, s), 0 88 (9H, s), 0.10 (6H, s).

12:

IR (CHCl$_3$): 3410, 1755, 1715, 1550 cm$^{-1}$.

$^1$H NMR (CDCl$_3$)δ: 7.40 (5H, m), 5.38 (2H, s), 5.26 (2H, s), 4 40 (1H, m), 4.10 (1H, dd, J=4,10), 3.80 (1H, dd, J=6,10), 1.46 (9H, s), 0.88 (9H, s), 0.06 (6H, s).

EXAMPLE 11

Preparation of 3-hydroxy-2S-tert-butyloxycarbonylamino-[5-(1-benzylacetate)tetrazolyl]propanamide (14)

By a like procedure as Example 15 below, 14 was prepared from 12 (85%).

EXAMPLE 12

Preparation of 3S-tert-butyloxycarbonylamino-1-[5-(1-benzylacetate)-tetrazolyl]azetidin-2-one (15)

By a like procedure as Example 16 below, 15 was prepared from 14 (59%):

IR (CHCl$_3$): 1790, 1760, 1715 cm$^{-1}$.

$^1$HMR (CDCl$_3$)δ: 7.36 (5H, m), 5.70 (1H, d, J=17.5), 5.48 (1H, d, J=17.5), 5.24 (1H, d, J=12), 5.16 (1H, d, J=12), 4.79 (1H, br s), 4.1 (2H, m), 1.46 (9H, s).

EXAMPLE 13

Preparation of 3S-phenylacetamido-1-[5-(1-benzyl.acetate)tetrazolyl]azetidin-2-one (16)

By a like procedure as Example 17 below, 16 was prepared from 15 (36%):

IR (CHCl$_3$): 1795, 1770, 1685 cm$^{-1}$.

$^1$H NMR (CDCl$_3$)δ: 7.34 (10H, m), 5.98 (1H, d, J=6.5), 5.72 (1H, d, J=17.5), 5.48 (1H, d, J=17.5), 5.28 (1H, d, J=12), 5.14 (1H, d, J=12), 4.74 (1H, ddd, J=3.5, 6.5, 7.0), 4.12 (1H, dd, J=6.5, 6.5), 4.04 (1H, dd, J=3.5, 7), 3.66 (2H, s).

EXAMPLE 14

Preparation of potassium 3S-phenylacetamido-1-[5-(1acetate)tetrazolyl]azetidin-2-one (17)

By a like procedure as Example 18 below, 17 was prepared from 16 (30%):

IR (KBr): 1785 cm$^{-1}$.

$^1$H NMR (D$_2$O)δ: 7.4 (5H, m), 5.35 (1H, d, J=16), 5.20 (1H, d, J=16), 5.15 (1H, m), 4.24 (1H, dd, J=5.5, 6.5), 4.08 (1H, dd, J=3.5, 5.5), 3.72 (2H, s).

EXAMPLE 15

Preparation of 3-hydroxy-2S-tert-butyloxycarbonylamino-[5-(2-benzylacetate)tetrazolyl]propanamide (18)

Hydrofluoric acid (24.5M, 0.20 ml, 5.0 mmol) was added to a solution of 13 (0.891 g, 1.67 mmol) in 8 ml acetonitrile at 0°. The mixture was allowed to warm to 25° and stir for 3 hours. dilution with 200 ml ethyl acetate and washing with solutions of 10% sodium bisulfate, saturated sodium bicarbonate and saturated sodium chloride was followed by drying over magnesium sulfate. After filtration and evaporation under vacuum, 0.710 g (98%) 18 remained as a white solid:

$^1$H NMR (CDCl$_3$).δ: 9.82 (1H, br s), 7.40 (5H, s), 5.77 (1H, J=7), 5.43 (2H, s), 5.28 (2H, s), 4.44 (1H, m) 4.29 (1H, dd, J=3, 11.5), 3.79 (1H, dd, J=4.5, 11.5), 1.49 (9H, s).

EXAMPLE 16

Preparation of 3S-tert-butyloxycarbonylamino-1-[5-(2-benzylacetate)-tetrazolyl]azetidin-2-one (19)

Diisopropylazodicarboxylate (0.41 g, 2.0 mmol) was added to a solution of 18 (0.710 g, 1.69 mmol), triphenylphosphine (0.53 g, 2.0 mmol) and 60 ml dry tetrahydrofuran at 0°. The solution was allowed to warm to 25° and stirred for 5 hours, before being diluted with 80 ml ethylacetate and washed with solutions of 10% sodium bisulfate, saturated sodium bicarbonate and saturated sodium chloride. Drying over magnesium sulfate and filtering was followed by evaporation under vacuum. The solid residue was chromatographed on silica gel and recrystallized to give 0.390 g (57%) 19, m.p. 188°-90°:

IR (CHCl$_3$) 3460, 1790, 1765, 1720, 1560 cm$^{-1}$.

$^1$H NMR (CDCl$_3$) δ: 7.41 (5H, br s), 4.41 (2H, s), 4.27 (2H, s), 5.06 (1H, m), 4.22 (1H, m), 4.02 (1H, dd, J=3.5, 6), 1.46 (9H, s). Mass Spec: 347, 329.

EXAMPLE 17

Preparation of 3S-phenylacetamido-1-[5-(2-benzylacetate)tetrazolyl]azetidin-2-one (20)

Trifluoroacetic acid (2 ml) was added to a solution of 19 (0.109 g, 0.271 mmol) and 5 ml dichloromethane at −5°. The solution was allowed to warm to 10° and stir for 3 hours. The volatiles were removed under a stream of nitrogen and under vacuum. Several milliliters of toluene were added to the residue and evaporated under vacuum. After repeating this toluene treatment, the residue was dissolved in 2 ml dichloromethane and cooled to −15°. Pyridine (0.13 ml, 1.6 mmol) and phenylacetylchloride (0.054 ml, 0.41 mmol) were added. After storage of the solution at −15O° for 3 days, it was diluted with 50 ml ethylacetate and washed with solutions of 5% potassium dihydrogenphosphate, saturated sodium bicarbonate, and saturated sodium chloride. The organic phase was dried over magnesium sulfate, filtered, evaporated under vacuum and chromatographed on silica gel to give 0.095 g (83%) 20 as a white solid; m.p. 135°:

[α]$_D^{25}$ = +36.8° (C=1, CHCl$_3$)

IR(CHCl$_3$): 3940, 1790, 1765, 1680, 1560, 1560 cm$^{-1}$.

$^1$H NMR (CDCl$_3$).δ: 7.40–3.30 (10H, m), 6.08 (1H, d, J=7), 5.40 (2H, s), 5.23 (2H, s), 5.09 (1H, ddd, J=3, 6, 7), 4.18 (1H, dd, J=6,6), 3.95 (1H, dd, J=3,6), 3.67 (2H, s).

EXAMPLE 18

Preparation of potassium 3S-phenylacetamido-1-[5(2-acetate)tetrazolyl]azetidin-2-one (21)

A mixture of 20 (0.037 g, 0.088 mmol), 55 mg 10% palladium on carbon, 1 ml tetrahydrofuran, 1 ml ethanol, 1 ml water, and 0.5 ml pH 7, 0.1M potassium dihydrogenphosphate/dipotassium hydrogenphosphate buffer was hydrogenated at 45 psi hydrogen for 1.5 hours. The mixture was filtered, washing with water, and evaporated to a volume of 1 ml. Reverse-phase preparative thin-layer chromatography (4% ethanol in water) gave 0.015 mg (47%) 21 as a white solid after eluting with 15 ml acetonitrile: water/4:1 and lyophilization:

IR(KBr): 3400 broad, 1775, 1700 broad cm$^{-1}$.

$^1$H NMR (D 0)δ:7.36 (5H, m), 5.27 (2H, s), 5.08 (1H, dd, J=3,5.5), 4.20 (1H, dd, J=5.5, 5.5), 3.99 (1H, dd, J=3,5.5), 3.68 (2H, s).

EXAMPLE 19

Preparation of tert-butyldimethylsilyl-3R-tert-butylmethylsilyloxy-3-methyl-2S-tert-butyloxycarbonylaminopropanoate (23)

A mixture of N-tert-butyloxycarbonyl-L-threonine 22 (8.00 g, 0.036 mol), tert-butyldimethylchlorosilane (11.56 g, 0.076 mol), imidazole (6.13 g, 0.09 mol), and 100 ml dry dimethylformamide was stirred at 22° for 3 days. After most of the solvent was removed under vacuum, the residue was diluted with 350 ml diethylether and washed with 200 ml solutions of 5% potassium dihydrogen phosphate, and saturated sodium chloride. The organic phase was dried over magnesium sulfate, filtered, and evaporated under vacuum to give 14.89 g (92%) 23 as a clear oil:

$^1$H NMR (CDCl$_3$)δ: 5.18 (1H, br d), 4.45 (1H, m), 4.16 (1H, m), 1.44 (9H, s), 1.22 (3H, d, J=6.5), 0.96 (9H, s), 0.93 (9H, s), 0.13 (3H, s), 0.09 (3H, s), 0.06 (3H, s), 0.02 (3H, s).

EXAMPLE 20

Preparation of (3R)-3-tert-butyldimethylsilyloxy-3-methyl-2S-tert-butyloxycarbonylamino-(5-tetrazolyl) propanamide (24)

Dicyclohexylcarbodiimide (8.24 g, 0.040 mol), 1-hydroxybenzotriazole (5.40 g, 0.040 mol), 23 (14.87 g, 0.033 mol), 3.2 ml pyridine, and 175 ml dry tetrahydrofuran were stirred at 23° for one hour and 5-aminotetrazole (4.20 g, 0.05 mol) was then added. After stirring at 23° for 18 hours, the mixture was filtered through diatomaceous earth, washing with 100 ml ethyl acetate. After most of the solvent was removed under vacuum, the residue was diluted with 250 ml ethylacetate and 250 ml diethylether and washed with solutions of 10% potassium bisulfate and saturated sodium chloride. The organic phase was dried over magnesium sulfate, filtered and evaporated under vacuum to give 18.13 g (>100%) 24 as a crisp, white foam. Analysis by proton NMR (nuclear magnetic resonance) showed the presence of about 10% 1-hydroxybenzotriazole:

IR (CHCl$_3$): 3400, 1705 cm$^{-1}$.

$^1$H NMR (CDCl$_3$)δ: 6.09 (1H, br d), 4.72 (1H, m), 4.56 (1H, m), 1.52 (9H, s), 1.41 (3H, d, J=6.5), 0.86 (9H,s), 0.15 (3H, s), 0.11 (3H, s).

EXAMPLE 21

Preparation of 3-tertbutyldimethylsilyloxy-2S-tertbutyloxycarbonylamino-[5-(2-triphenylmethyl)tetrazolyl]propanamide (25)

A mixture of 4 (17.07 g, 0.044 mol), triphenylmethyl chloride (13.55 g, 0.049 mol), 4-dimethylaminopyridine (1.08 g, 0.0088 mol), triethylamine (9.2 ml, 0.066 mol), and 200 ml dry N,N-dimethylformaide was stirred at 25° for 18 hours. The solvent was removed at 35° under vacuum and the residue was diluted with 800 ml ethyl acetate/diethyl ether, 1/1. After washing with solutions of 5% potassium dihydrogenphosphate, saturated sodium bicarbonate and saturated sodium chloride, the organic phase was dried over magnesium sulfate and filtered. The solvent was removed under vacuum to yield 26.56 (95%) 25 as a oil, judged pure by TLC and NMR:

IR (CHCl$_3$): 1710 cm$^{-1}$.

$^1$H NMR (CDCl$_3$)δ: 7.34 (15H, m), 5.44 (1H, br d), 4.38 (1H, m), 4.12 (1H, dd, J=4, 10), 3.71 (1H, dd, J=8, 10), 1.46 (9H, s), 0.88 (9H, s), 0.08 (6H, s).

EXAMPLE 22

Preparation of 3-hydroxy-2S-tert-butyloxycarbonylamino-[5-(2-triphenylmethyl)tetrazolyl]propanamide (27)

To a solution of 25 (4.00 g, 0.0080 mol) and 150 ml dry tetrahydrofuran was added tetra-n-butylammonium fluoride (12.0 ml, 0.012 mol, 1M in tetrahydrofuran). After stirring at 23° for 17 hours, the solution was diluted with ethyl acetate and washed with water and saturated sodium chloride. The organic phase was dried over magnesium sulfate, filtered, and evaporated under vacuum to give 4.92 g (>100%) 27 as an off-white foam:

$^1$H NMR (CDCl$_3$) : 7.48 (15H, m), 5.94 (1H, br d), 4.51 (1H, m), 3.82 (1H, dd, J=5,12), 3.4 (1H, m), 1.52 (9H, s).

EXAMPLE 23

Preparation of 3S-tert-butyloxycarbonylamino-1-[5-(2-triphenylmethyl)tertrazolyl]azetidin-2-one (28)

Diisopropylazodicarboxylate (2.01 ml, 0.011 mol) was added to a solution of 27 (5.02 g, 0.010 m), triphenylphosphine (2.80 g, 0.011 mol), and 100 ml dry tetrahydrofuran and the solution was stirred at 24° for 18 hours. The solvent was removed under vacuum and the residue was chromatographed on silica gel to give 2.11 g (43%) 28 as a white foam:

IR (CHCl$_3$) 1785, 1725 cm$^{-1}$.

$^1$H NMR (CDCl$_3$) δ: 7.22 (15H, m), 5.22 (1H, m), 5.03 (1H, m), 4.15 (1H, m), 3.92 (1H, m), 1.46 (9H, s).

EXAMPLE 24

Preparation of 3S-tert-butyloxycarbonylamino-1-[5-tetrazolyl)azetidin-2-one (29)

Formic acid (2 ml) was added to a solution of 28 (0.200 g, 0.40 mmol) and 6 ml acetone and the solution was stirred at 23° for 16 hours. Dilution with 20 ml water was followed by adjustment of the pH to 8 with 2.5 N sodium hydroxide. After washing with three 30 ml portions of dichloromethane, the aqueous phase was acidified to pH 3 with 2.5N hydrochloric acid. Extraction with four 40 ml portions of ethyl acetate and drying of the combined organic phases was followed by filtration. Evaporation of the solvent gave 0.072 g (70%) 29 as a white foam:
IR (CH$_3$CN): 1790, 1715 cm$^{-1}$.
$^1$H NMR (acetone d6)δ: 7.3 (1H, br d), 5.16 (1H, br s), 4.24 (1H, dd, J=6, 6), 4.03 (1H, dd, J=3.5, 6), 1.43 (9H, s).

EXAMPLE 25

Preparation of 3S-ammonium-1-(5-tetrazolyl)azetidin-2-one trifluoroacetate (30)

Trifluoroacetic acid (0.75 ml) was added to 29 (0.087 g, 0.34 mmol) and 1 ml dichloromethane at 0°. The solution was allowed to warm to 23° and stir for 1.5 hours. The volatiles were removed under a stream of nitrogen. Toluene (3 ml) was added and evaporated under vacuum. Trituration with diethylether gave 0.076 g (83%) 30 as a white solid:
IR (KBr) 1790 cm$^{-1}$.
$^1$H NMR (D2O) δ: 4.92 (1H, m), 4.59 (1H, dd, J=2,7), 4.30 (1H, t, J=6,6).

EXAMPLE 26

Preparation of 3S-[(1-benzylpyridinium)-4-amino]-1-(5-tetrazolyl)-azetidin-2-one (31)

A mixture of 30 (0.012 g, 0.077 mmol) and 1 ml water was cooled to 0°. The pH was adjusted to 8.4 with 0.30 ml 1.75 N sodium hydroxide. A mixture of 1-benzyl-4-fluoropyridinium bromide (0.031 g, 0.12 mmol) and 1 ml water was added and the resulting suspension was warmed to 23°. After stirring for 4 hours, evaporation under vacuum gave a residue which was chromatographed by reverse phase preparative TLC (35% acetonitrile in water). A band at R$_f$0.6 was eluted with 80% acetonitrile in water and evaporated and lyophilized to give 9.3 mg (37%) 31 as a white solid:
IR (KBr): 1770, 1640, 1530 cm$^{-1}$.

$^1$H NMR (D2O)δ: 8.2 (2H, br s), 7.41 (5H, m), 7.03 (2H, m), 5.41 (1H, m), 5.39 (2H, s), 4.33 (1H, dd, J=6,6.5), 3.92 (1H, dd, J=2.5, 6.5).

EXAMPLE 27

Preparation of (2S,3R)-3-tert-butyldimethylsilyloxy-3-methyl-2-tert-butyloxycarbonylamino-[5-(2-triphenylmethyl)tetrazolyl]propanamide (26)

By a like procedure as Example 21, 26 was prepared from 24 (38%):
$^1$H NMR (CDCl$_3$)δ: 7.1–7.40 (15H, m), 5.52 (1H, m), 4.47 (1H, m), 4.32 (1H, m), 1.47 (9H, s), 1.17 (3H, d, J=6), 0.87 (9H, s), 0.10 (6H, s).

EXAMPLE 28

Preparation of (2S,3R)-3-hydroxy-3-methyl-2-tertbutyloxycarbonylamino-[5-(2-triphenylmethyl)tetrazolyl]propanamide (32)

By a like procedure as Example 22, 32 was prepared from 26:

$^1$H NMR (CDCl$_3$)δ: 7.28 (15H, m), 5.60 (1H, d, J=8), 4.55 (1H, m), 4.32 (1H, m), 3.38 (1H, m), 1.46 (9H, s), 1.23 (3H, d, J=6).

EXAMPLE 29

Preparation of (3S,4S)-3-tert-butyloxycarbonylamino-4-methyl-1-[5-(2-triphenylmethyl)tetrazolyl]azetidin2-one (33)

By a like procedure as Example 23, 33 was prepared from 32 (54%):
IR (CHCl$_3$):δ 1785 cm$^{-1}$.
$^1$H NMR (CDCl$_3$) : 7.25 (15H, m), 5.27 (1H, d, J=8), 4.53 (1H, m), 4.23 (1H, m), 1.59 (3H, d, J=6), 1.43 (9H, s).

EXAMPLE 30

Preparation of (3S,4S)-3-tert-butyloxycarbonylamino-4-methyl-1-(5-tetrazolyl)azetidin-2-one (34)

By a like procedure as Example 24, 34 was prepared from 35 (32%):
$^1$H NMR (acetone d6)δ: 7.0 (1H, br s), 4.66 (1H, m), 4.50 (1H, dq, J=3,6), 1.70 (3H, d, J=6), 1.42 (9H, s).

EXAMPLE 31

Preparation of (3S,4S)-3-ammonium-4-methyl-1-(5-tetrazolyl)azetidin-2-one trifluoroacetate (35)

By a like procedure as Example 25, 35 was prepared from 34 (60%):
$^1$H NMR (D 0)δ: 4.9 (1H, m), 3.9 (1H, m), 1.59 (3H, d, J=6).

EXAMPLE 32

Preparation of (3S,4S)-3-[(1-benzylpyridinium)-4-amino]-4-methyl-1-(5-tetrazolyl)-azetidin-2-one (36)

By a like procedure as Example 26, 36 was prepared from 35 (16%):
IR (KBr): 1770, 1645, 1520 cm$^{-1}$.
$^1$H NMR (D 0)δ: 8.22 (2H, br s), 7.46 (5H, m), 7.04 (2H, d, J=8), 5.41 (2H, s) 5.06 (1H, d, J=2.5), 4.42 (1H, dq, J=2,5, 6), 1.67 (3H, d, J=6).

EXAMPLE 33

Preparation of 3S-[2-(2-aminothiazol-4-yl)-2-(Z)-methoxyiminoacetamido)-1-(5-tetrazolyl)-azetidin-2-one (37)

Isobutylchloroformate (0.019 ml, 0.144 mmol) was added to a solution of 2-(2-triphenylmethylaminothiazol-4-yl)-2-methoxyiminoacetic acid (0.058 g, 0.131 mmol), N-methylmorpholine (0.016 ml, 0.144 mmol), and 1.5 ml dry tetrahydrofuran at −15°. After one hour, a solution of 30 (0.053 g, 0.096 mmol), N-methylmorpholine (0.016 ml, 0.144 mmol), and 1.5 ml dry tetrahydrofuran was added and the resulting solution was allowed to warm to 23° and stir for 19 hours. The solvent was removed under a stream of nitrogen and diluted with 50 ml ethyl acetate. After washing with 5% potassium dihydrogenphosphate and saturated sodium chloride solutions, the organic phase was dried over magnesium sulfate, filtered, and evaporated under vacuum. The residue was dissolved in 1 ml 97% formic acid and stirred at 23° for 3 hours. The solvent was removed under vacuum diluted with 10 ml water, and washed with two 30 ml solutions of 1:1, ethyl acetate:diethyl ether. The aqueous phase was evaporated under vacuum and chromatographed on HP-20 resin (a macroreticular polystyrene/divinylbenzene copolymer resin manufactured by Mitsubishi Chemical Co.), using 3% ethanol in water, to give 0.014 g (31%) 37 as a white solid after lyophilization.

IR (KBr): 1775 cm$^{-1}$.

$^1$H NMR (D2O)$\delta$: 7.02 (1H, s), 5.32 (1H, dd, J=3,6), 4.29 (1H, dd, J=6, 6.5), 4.06 (1H, dd, J=3, 6.5), 4.02 (3H, s).

EXAMPLE 34

Preparation of (3S,4S)-3-[2-(2-aminothiazol-4-yl)-2-(Z)-methoxyiminoacetamido)-4-methyl-1-(5-tetrazolyl)-azetidin-2-one (38)

By a like procedure as Example 33, 38 was prepared from 35 (22%):

IR (KBr): 1750, 1670 cm$^{-1}$.

$^1$H NMR (D2O)$\delta$: 6.9 (1H, s), 4.5 (1H, m), 4.06 (1H, m), 3.98 (3H, s), 1.62 (3H, d, J=6).

EXAMPLE 35

Preparation of (3S,4S)-4-methyl-3-[(Z)-2-(2-triphenylmethylaminothiazol-4-yl)-2-(2-tert-butylcarboxyprop-2oxyimino)acetamido]-1-(5-tetrazolyl)-azetidin-2-one (39)

Chlorodiphenylphosphate (0.028 ml, 0.134 mmol) was added to a solution of 2-(2-triphenylmethylaminothiazol-4-yl)-2-(2-tert-butylcarboxyprop-2-oxyimino)acetic acid (0.064 g, 0.112 mmol), triethylamine (0.023 ml, 0.167 mmol), and 2 ml dry acetonitrile at 0°. After one hour, a solution of 35 (0.032 g, 0.112 mmol), triethylamine (0.015 ml, 0.11 mmol) and 1 ml dry acetonitrile was added. The resulting solution was stirred at 24° for 18 hours. Dilution with ethyl acetate was followed by washing with 5% potassium dihydrogenphosphate and saturated sodium chloride solutions. The organic phase was dried over magnesium sulfate, filtered, and evaporated to give 0.082 g (100%) 39 as a pale yellow oil, judged pure by TLC, IR, and NMR:

IR (CHCl3): 1790, 1720, 1685 cm$^{-1}$.

$^1$H NMR (CDCl3)$\delta$: 8 84 (1H, d, J=8), 7.3 (15H, m), 6.85 (1H, s), 4.92 (1H, dd, J=2.5, 7), 4.40 (1H, m), 1.82 (3H, d, J=7), 1.43 (6H, s), 1.28 (9H, s).

EXAMPLE 36

Preparation of (3S,4S)-4-methyl-3-[(Z)-2-(2-aminothiazol-4-yl)-2-(2-carboxyprop-2-oxyimino)acetamido]-1-(5-tetrazolyl)-azetidin-2-one (40)

Trifluoroacetic acid (0.50 ml) was added to a −15° solution of 39 (0.047 g, 0.065 mmol) and 0.5 ml dichloromethane. After one hour, the solution was warmed to 23° and stirred for an additional hour before 2 ml toluene was added and volatiles were removed under a stream of nitrogen. Dilution with 10 ml water and washing with 20 ml of 1:1, ethyl acetate: diethyl ether was followed by evaporation under vacuum and chromatography by reverse phase preparative TLC (10% ethanol in water). Elution of a band of R$_f$ 0.9 with 80% acetonitrile in water gave 0.0043 g (16%) 40 as a white solid after lyophilization:

IR (KBr): 1765, 1700 br cm$^{-1}$.

$^1$H NMR (D2O)$\delta$: 6.98 (1H, s), 4.9 (1H, d, J=2.5), 4.5 (1H, dd, J=2.5, 6.5), 1.64 (3H, d, J=6.5), 1.47 (6H, s).

EXAMPLE 37

Preparation of Pharmaceutical Compositions

One such unit dosage from consists in mixing 120 mg of (3S,4S)-4-methyl-3-[(Z)-2-(2-amino-thiazol-4-yl)-2-(2-carboxyprop-2-oxyimino)acetamido]-1-(5-tetrazolyl)-azetidin-2-one with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules or compressed tablets and pills can also be prepared. The following examples are illustrative of the preparation of pharmaceutical formulations:

| TABLET | PER TABLET |
|---|---|
| (3S,4S)-4-methyl-3-[(Z)-2-(2-amino-thiazol-4-yl)-2-(2-carboxyprop-2-oxyimino)acetamido]-1-(5-tetrazolyl)-azetidin-2-one | 125 mg |
| Cornstarch, U.S.P. | 6 mg |
| Dicalcium Phosphate | 192 mg |
| Lactose, U.S.P. | 190 mg |
| Magnesium Stearate | 287 mg |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

The following formulations are prepared by combining the listed ingredients by standard techniques.

| PARENTERAL SOLUTION: Ampoule: | |
|---|---|
| (3S,4S)-4-methyl-3-[(Z)-2-(2-amino-thiazol-4-yl)-2-(2-carboxyprop-2-oxyimino)acetamido]-1-(5-tetrazolyl)-azetidin-2-one | 500 mg |
| Sterile water | 2 ml |
| OPHTHALMIC SOLUTION | |
| (3S,4S)-4-methyl-3-[(Z)-2-(2-amino-thiazol-4-yl)-2-(2-carboxyprop-2-oxyimino)acetamido]-1-(5-tetrazolyl)-azetidin-2-one | 100 mg |
| Hydroxypropylmethylcellulose | 5 mg |
| Sterile water | to 1 ml |
| OTIC SOLUTION | |
| (3S,4S)-4-methyl-3-[(Z)-2-(2-amino-thiazol-4-yl)-2-(2-carboxyprop-2-oxyimino)acetamido]-1-(5-tetrazolyl)-azetidin-2-one | 100 mg |
| Benzalkonium Chloride | 0.1 mg |
| Sterile water | to 1 ml |
| TOPICAL OINTMENT | |
| (3S,4S)-4-methyl-3-[(Z)-2-(2-amino-thiazol-4-yl)-2-(2-carboxyprop-2-oxyimino)acetamido]-1-(5-tetrazolyl)-azetidin-2-one | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound of the formula:

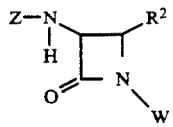

and the pharmaceutically acceptable salts thereof wherein $R^2$ is hydrogen, alkyl having 1 to 6 carbon atoms or carboalkoxy having 2 to 7 carbon atoms; and Z is

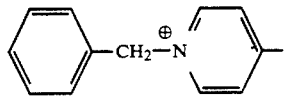

and W is

thus forming a zwitterion, or Z is

wherein $R^1$ is benzyl, phenyloxymethyl or

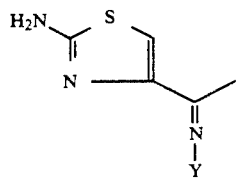

wherein
Y is alkoxy or substituted alkoxy having 1 to 6 carbon atoms wherein the substituent on the alkoxy group is —COOH; and
W is

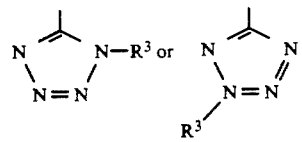

wherein $R^3$ is H, M or —CH$_2$COOM, wherein M is a pharmaceutically acceptable cation.

2. (3S, 4S)-4-methyl-3-[(Z)-2-(2-amino-thiazol-4-yl)-2-(2-carboxyprop-2-oxyimino)acetamido]-1-(5-tetrazolyl)-azetidin-2-one, according to claim 1.

3. 4S-methyl-3S-(2-(2-aminothiazol-4-yl)-2-(Z)-methoxy-iminoacetamido)-1-(5-tetrazolyl)-azetidin-2-one, according to claim 1.

4. 3S-(2-(2-aminothiazol-4-yl)-2-(Z)-methoxyimmino acetamido)-1-(5-tetrazolyl)-azetidin-2-one, according to claim 1.

5. An antibacterial pharmaceutical composition comprising an effective amount of a compound of claim 1 and a pharmaceutically acceptable carrier.

6. A method of treating bacterial infections in mammals comprising administering to an infected patient an antibacterial composition of claim 5.

* * * * *